(12) United States Patent  (10) Patent No.: US 8,137,363 B2
Cho  (45) Date of Patent: Mar. 20, 2012

(54) ELECTRICAL DERMABRASION DEVICE

(76) Inventor: Gyung Su Cho, Bucheon-si (KR)

( * ) Notice: Subject to any disclaimer, the term of this patent is extended or adjusted under 35 U.S.C. 154(b) by 787 days.

(21) Appl. No.: 11/587,742

(22) PCT Filed: Apr. 12, 2005

(86) PCT No.: PCT/KR2005/001060
§ 371 (c)(1),
(2), (4) Date: Nov. 13, 2006

(87) PCT Pub. No.: WO2005/109996
PCT Pub. Date: Nov. 24, 2005

(65) Prior Publication Data
US 2007/0225732 A1 Sep. 27, 2007

(30) Foreign Application Priority Data

Apr. 30, 2004 (KR) .................. 10-2004-0030805
Nov. 27, 2004 (KR) .................. 20-2004-0034154 U

(51) Int. Cl.
A61B 17/50 (2006.01)
(52) U.S. Cl. ........ 606/131; 451/344; 451/359; 451/451; 451/524
(58) Field of Classification Search .................. 606/131, 606/132; 604/289, 290; 132/73, 73.5, 73.6, 132/75.8, 76.4; 451/358, 359, 344, 451, 451/453, 456
See application file for complete search history.

(56) References Cited

U.S. PATENT DOCUMENTS

| 3,226,888 | A | * | 1/1966 | Erenyi | 451/494 |
| 3,256,648 | A | * | 6/1966 | Subonovich | 451/456 |
| 3,468,079 | A | * | 9/1969 | Kaufman | 451/510 |
| 3,906,940 | A | * | 9/1975 | Kawada | 601/6 |
| 4,667,447 | A | * | 5/1987 | Barton | 451/494 |
| 5,240,339 | A | * | 8/1993 | DeForest et al. | 401/207 |
| 5,357,717 | A | * | 10/1994 | Friel et al. | 451/494 |
| 5,609,516 | A | * | 3/1997 | Courson et al. | 451/456 |
| 5,795,216 | A | * | 8/1998 | Graves | 451/456 |
| 5,957,945 | A | * | 9/1999 | Bays | 606/180 |
| 6,139,553 | A | | 10/2000 | Dotan | |
| 6,423,078 | B1 | | 7/2002 | Bays et al. | |
| 6,500,183 | B1 | * | 12/2002 | Waldron | 606/131 |
| 6,629,983 | B1 | | 10/2003 | Ignon | |
| 2002/0177858 | A1 | * | 11/2002 | Sherman et al. | 606/131 |
| 2003/0060834 | A1 | | 3/2003 | Muldner | |
| 2004/0010268 | A1 | | 1/2004 | Gabehart | |
| 2004/0138680 | A1 | * | 7/2004 | Twitchell et al. | 606/131 |
| 2004/0143273 | A1 | * | 7/2004 | Winitsky | 606/131 |
| 2004/0181241 | A1 | * | 9/2004 | Jo et al. | 606/131 |
| 2006/0116694 | A1 | * | 6/2006 | Hogan et al. | 606/131 |
| 2006/0253125 | A1 | * | 11/2006 | Ignon | 606/131 |
| 2006/0276806 | A1 | * | 12/2006 | Martinez Zunino | 606/131 |
| 2007/0079841 | A1 | * | 4/2007 | Geils | 132/76.4 |
| 2007/0089758 | A1 | * | 4/2007 | Koutscumbos | 132/76.4 |
| 2008/0275468 | A1 | * | 11/2008 | Chuang et al. | 606/131 |

FOREIGN PATENT DOCUMENTS

| DE | 20211277 U1 | 1/2003 |
| FR | 2 728 777 | 7/1996 |
| WO | WO 03/024518 A2 | 3/2003 |
| WO | WO 2004/002339 A1 | 1/2004 |

* cited by examiner

Primary Examiner — Tuan Nguyen
Assistant Examiner — Thomas McEvoy
(74) Attorney, Agent, or Firm — Hoffmann & Baron, LLP

(57) ABSTRACT

An electrical dermabrasion device (10) for exfoliating a foot includes a hollow main body (12); an abrasion unit (32, 42) connected to the main body (12), for exfoliating the foot; and a driving unit (14, 16, 18) incorporated in a hollow portion of the main body (12), for rotating the abrasion unit (32, 42).

26 Claims, 14 Drawing Sheets

[Fig. 1]
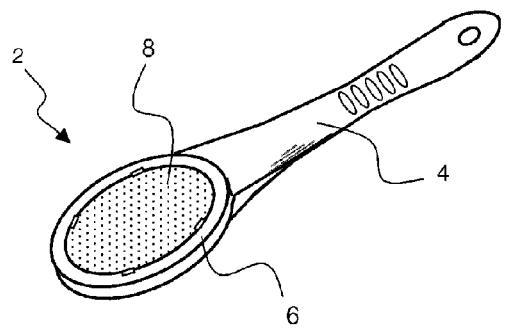
[Fig. 2]
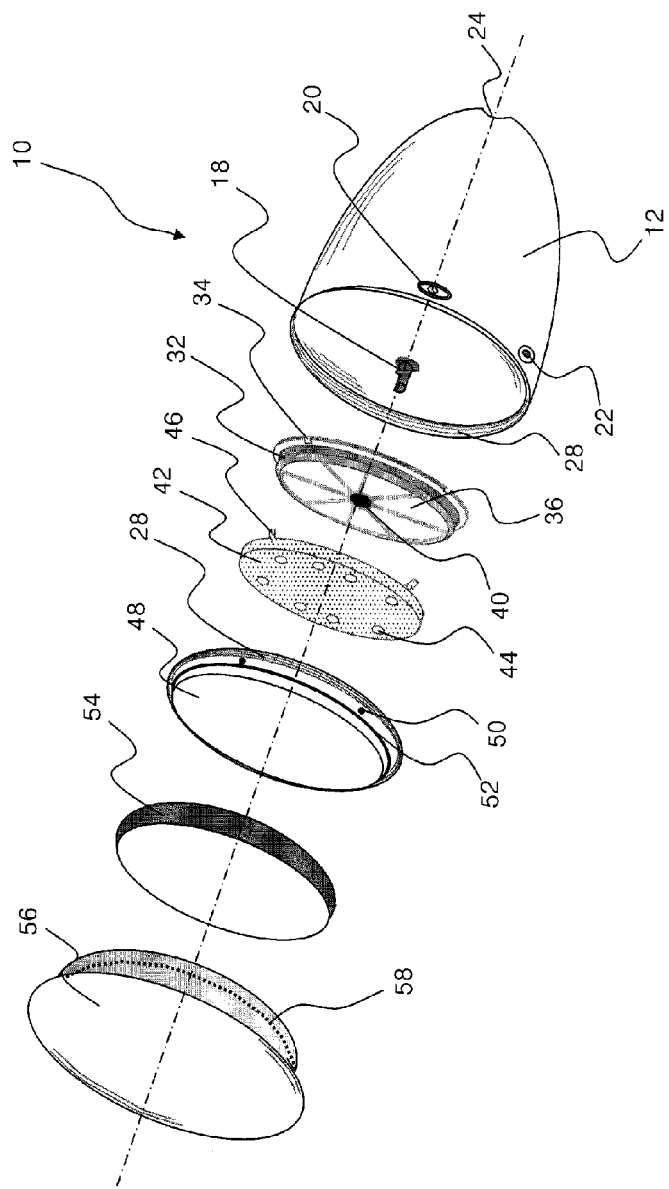

[Fig. 3]
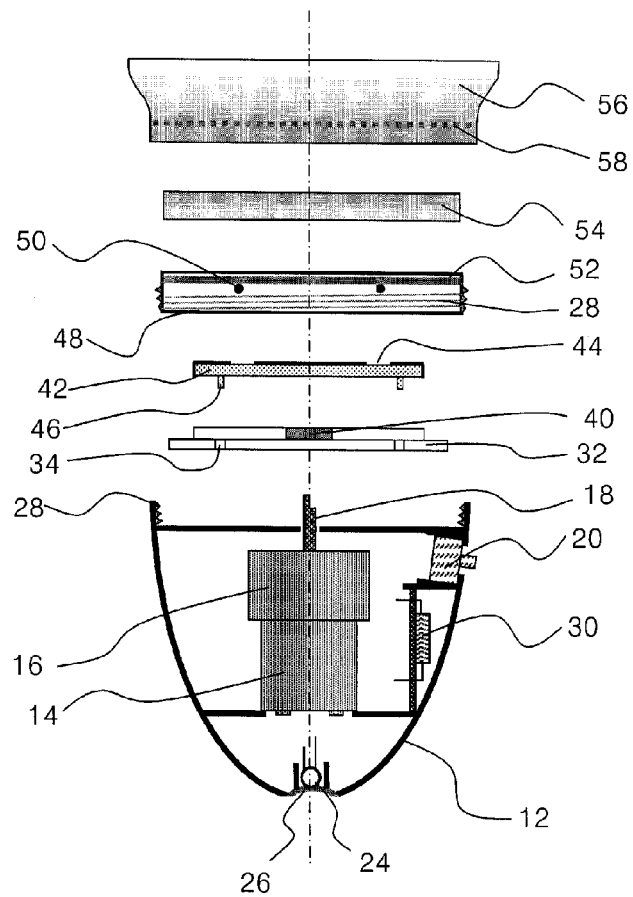
[Fig. 4]
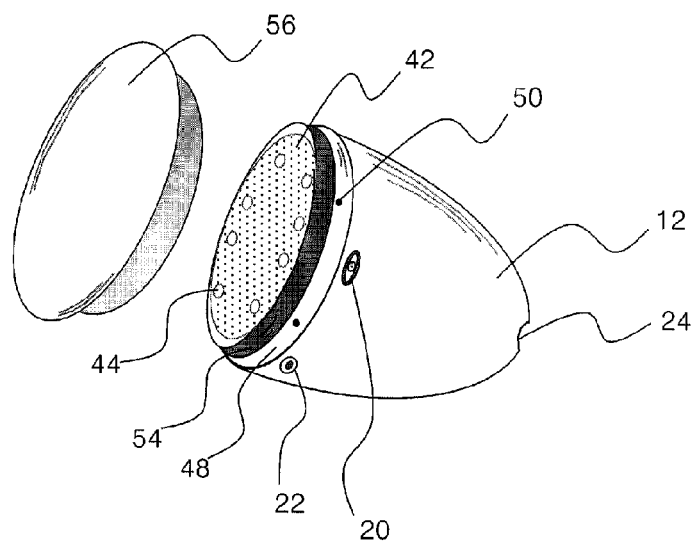

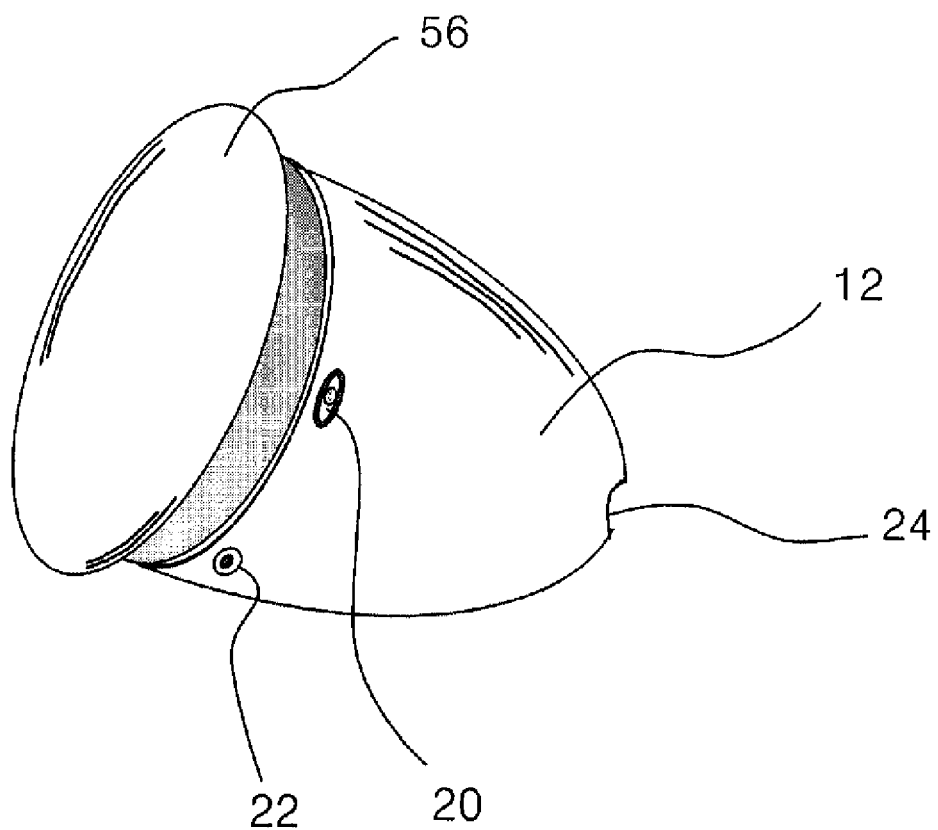
[Fig. 5]

[Fig. 6]
(A)
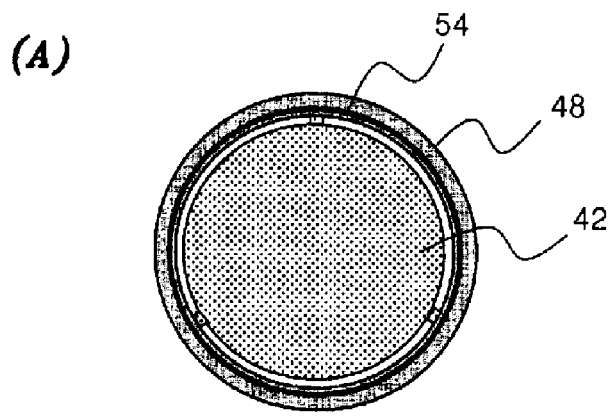
(B)
(C)
(D)

[Fig. 7]
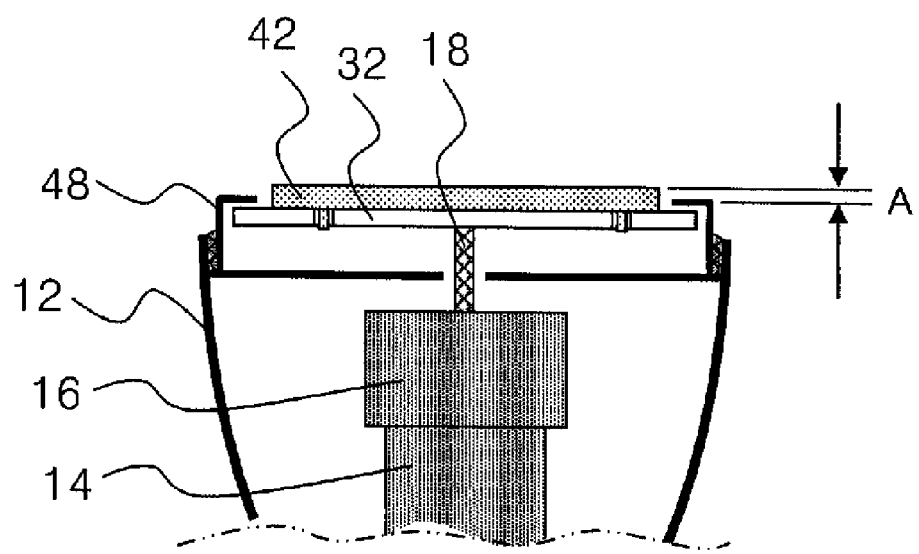
[Fig. 8]
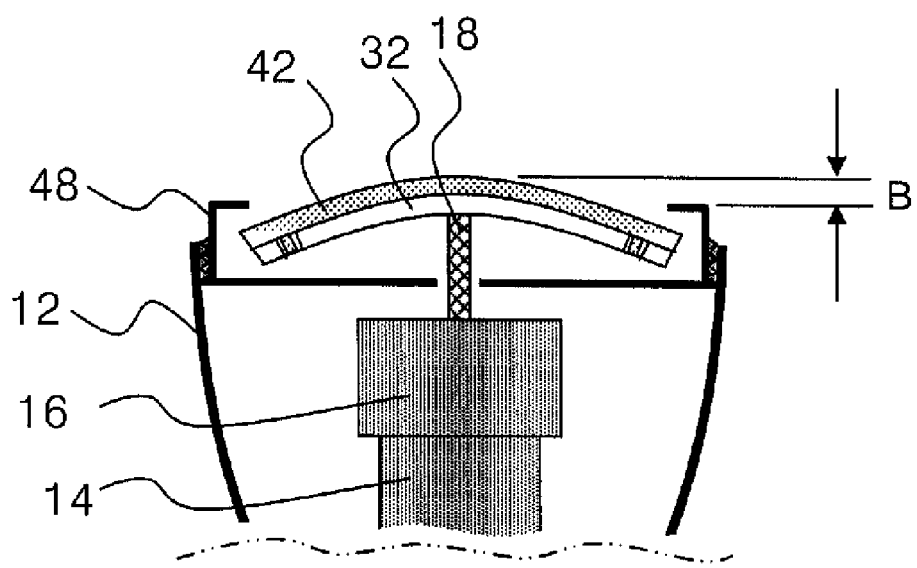

[Fig. 9]
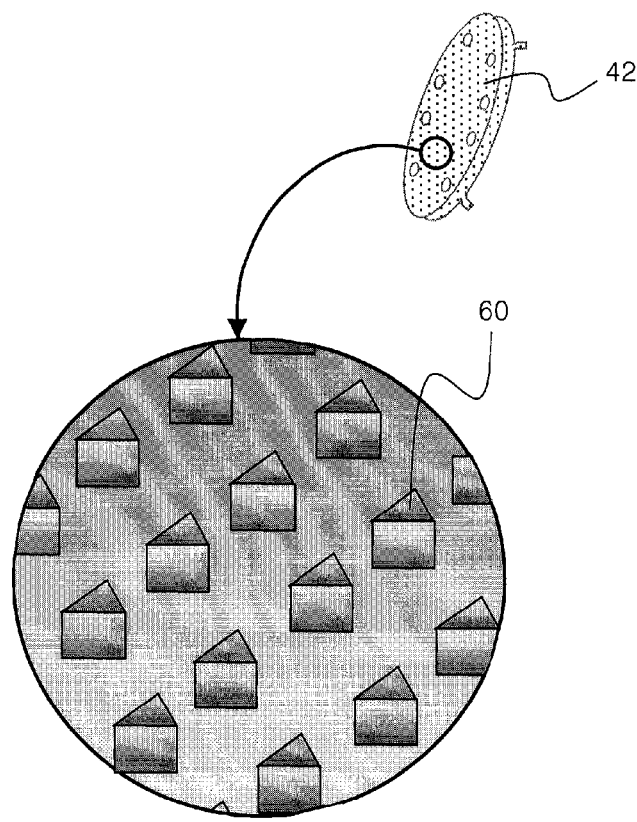
[Fig. 10]
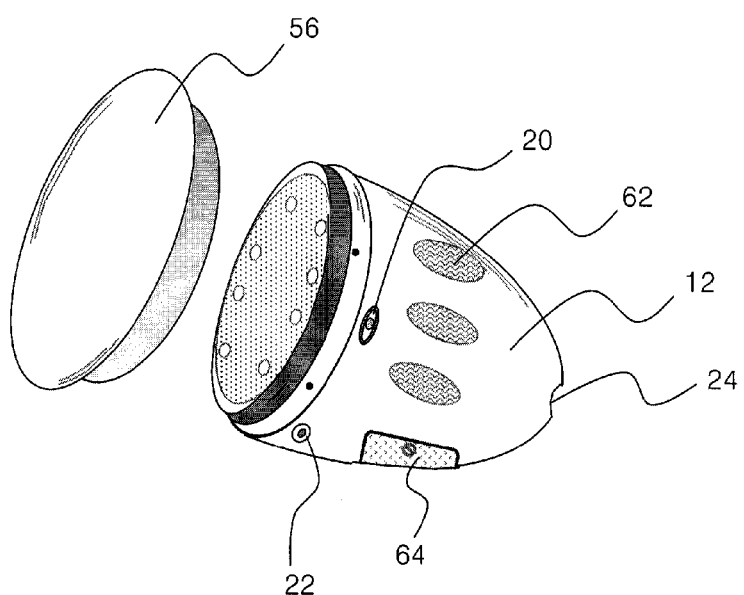

[Fig. 11]
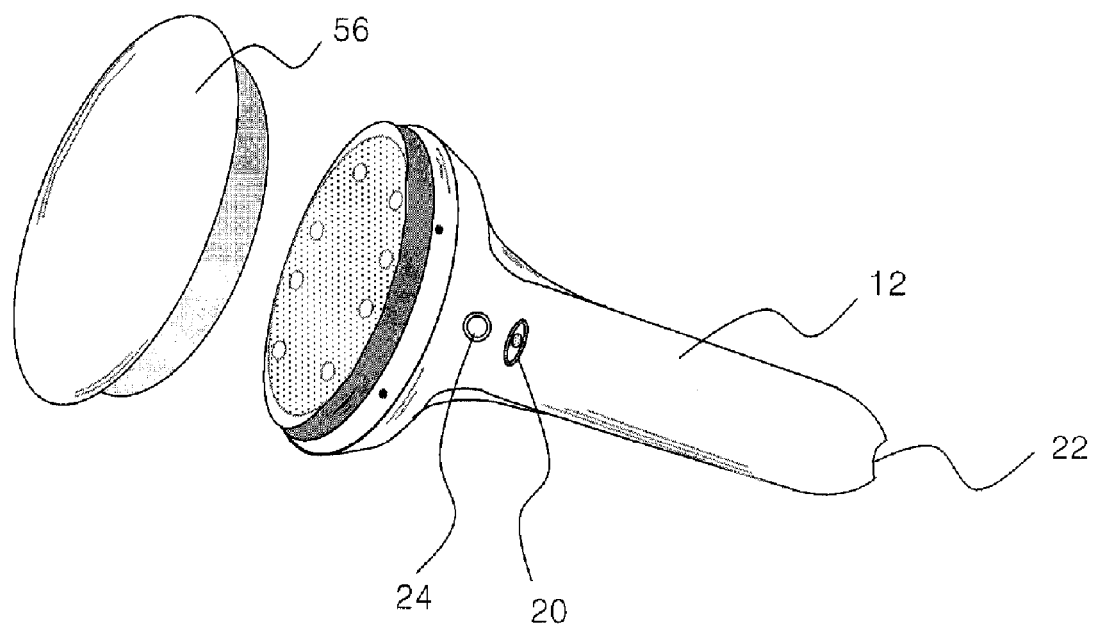

[Fig. 12]
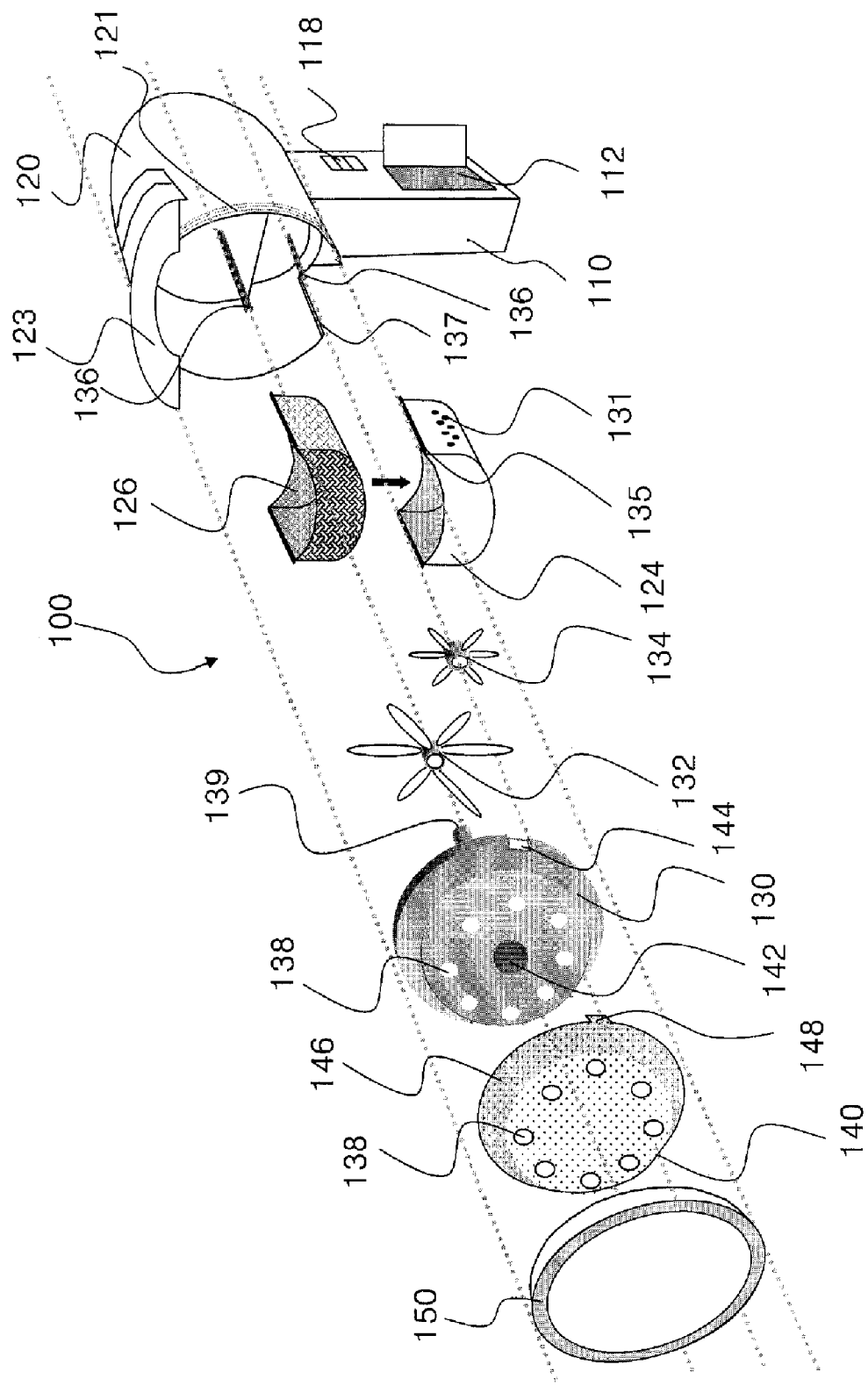

[Fig. 13]
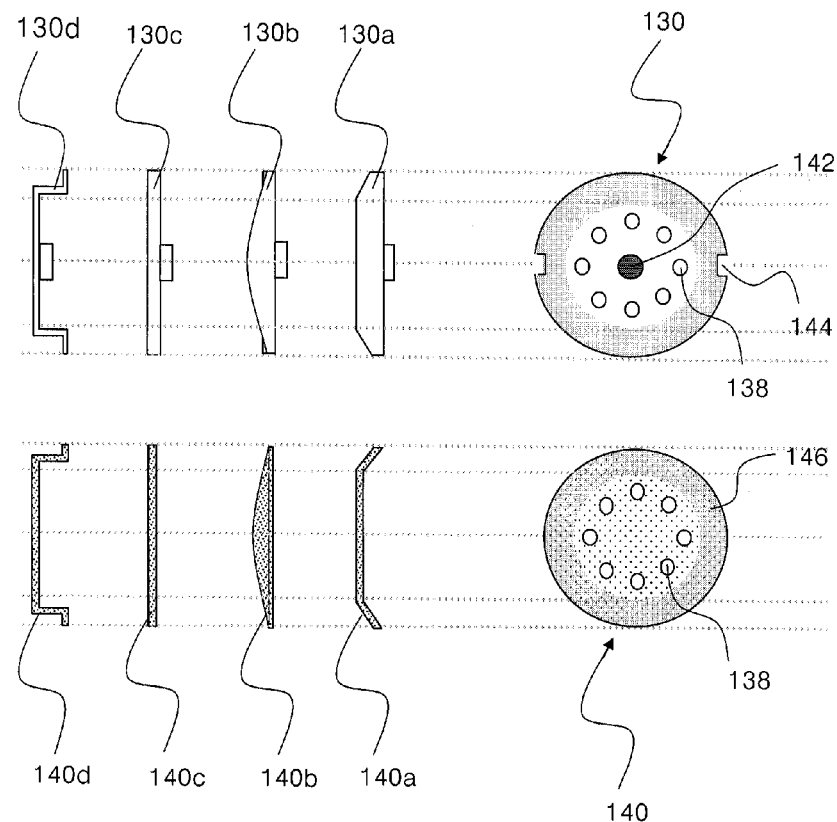
[Fig. 14]
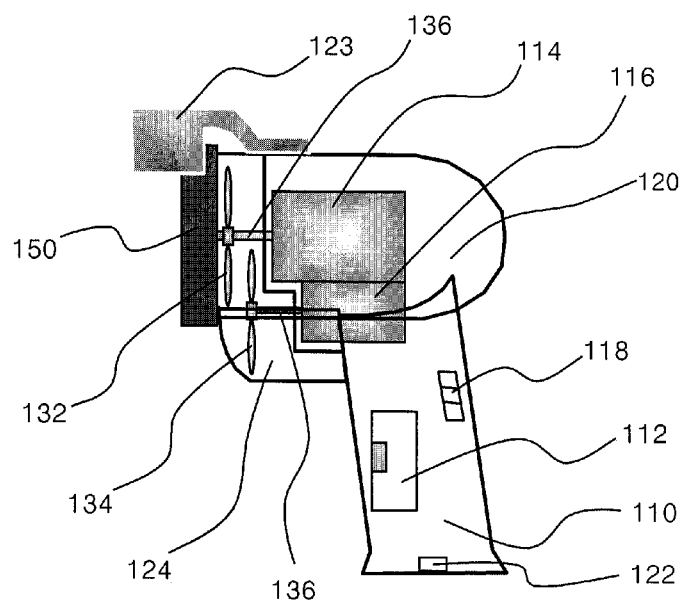

[Fig. 15]
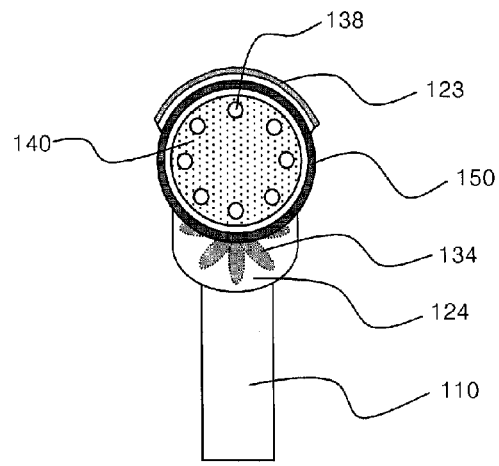
[Fig. 16]
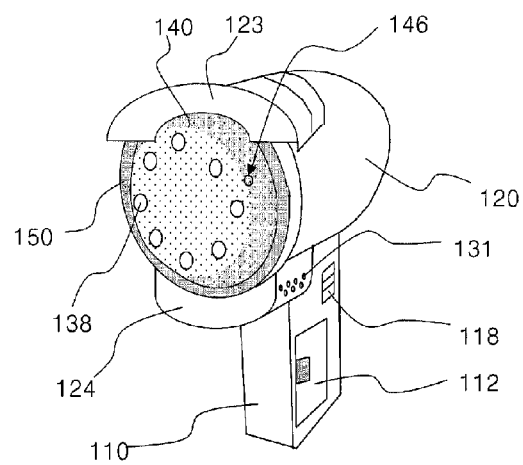
[Fig. 17]
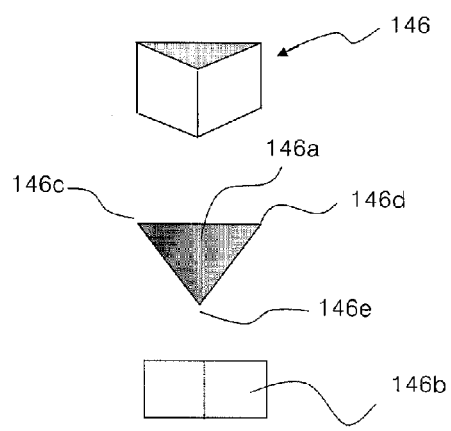

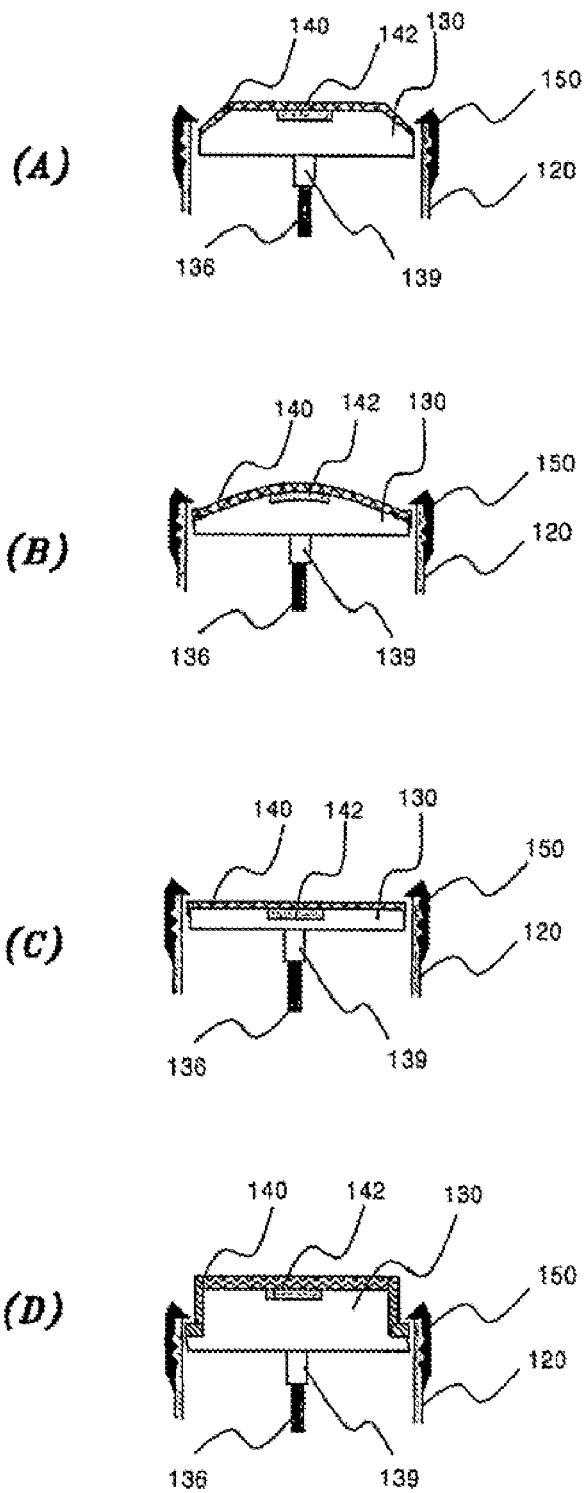
[Fig. 18]

[Fig. 19]
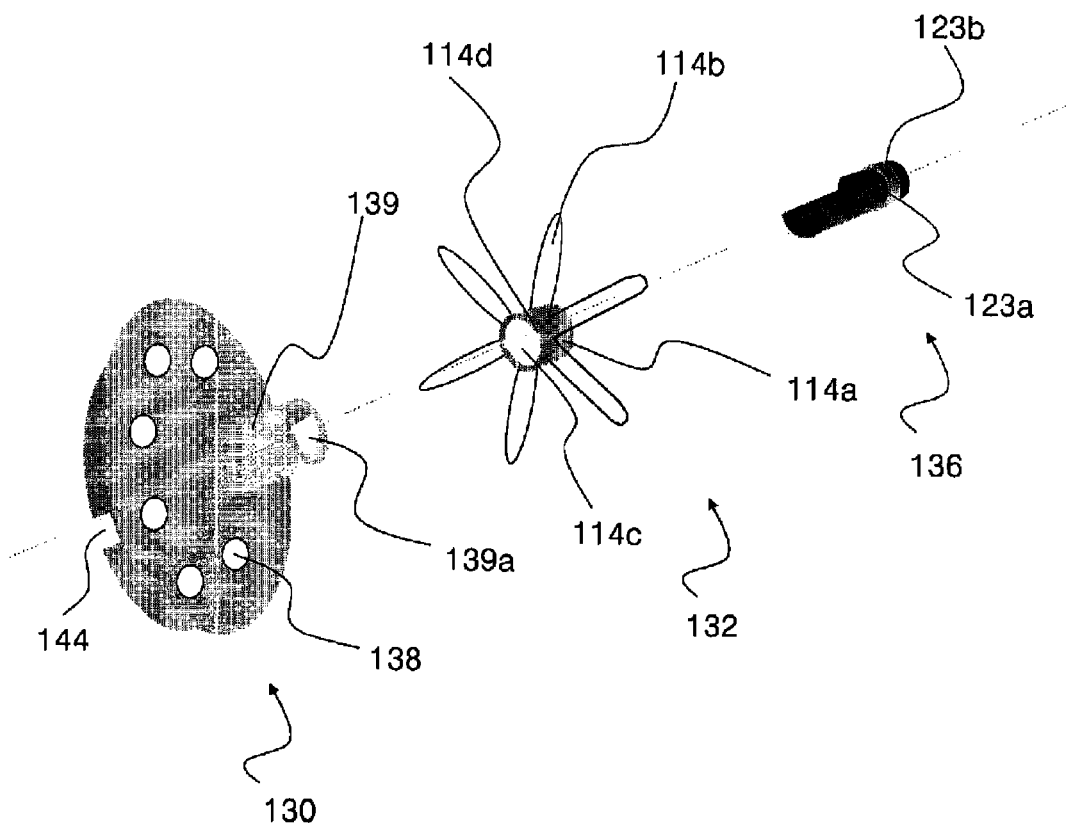
[Fig. 20]
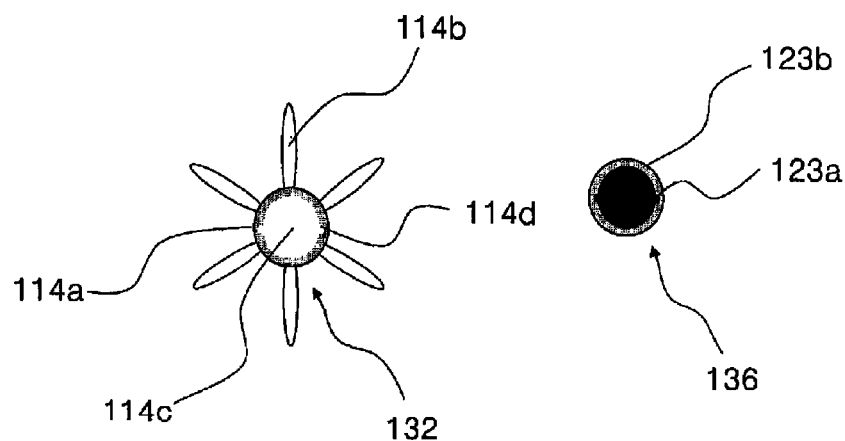

[Fig. 21]
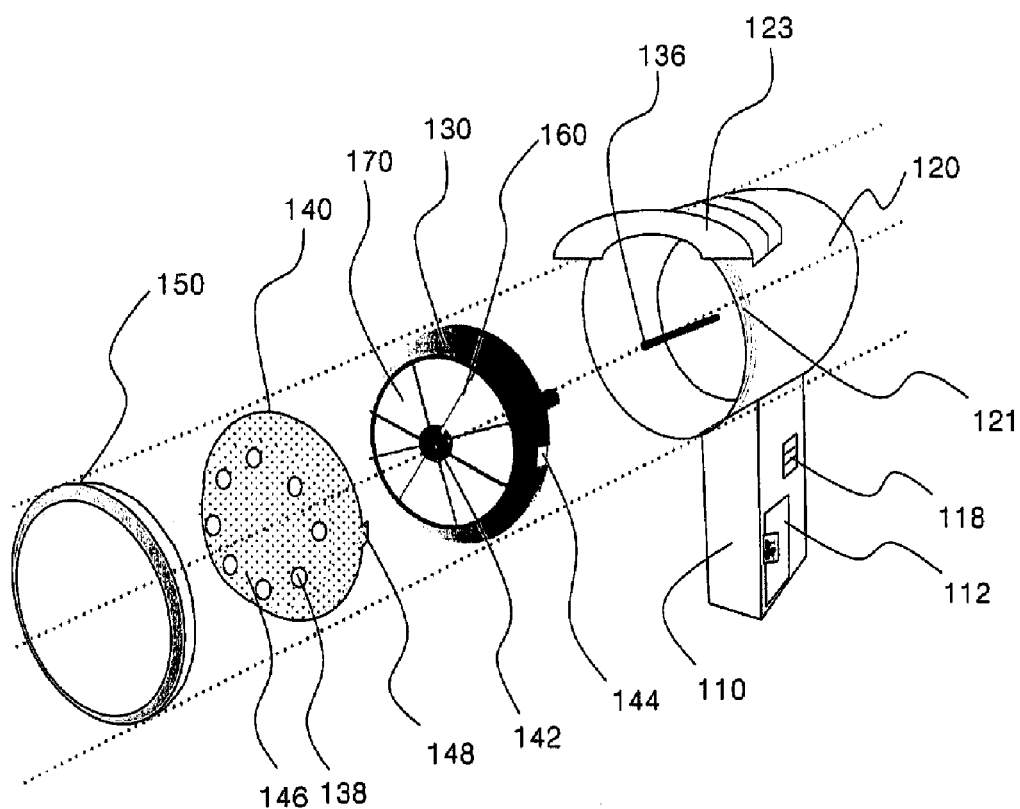
[Fig. 22]
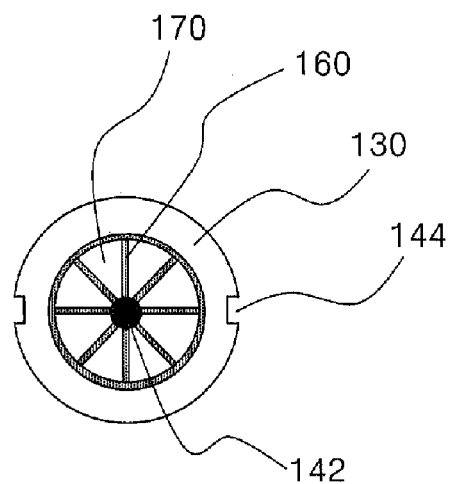

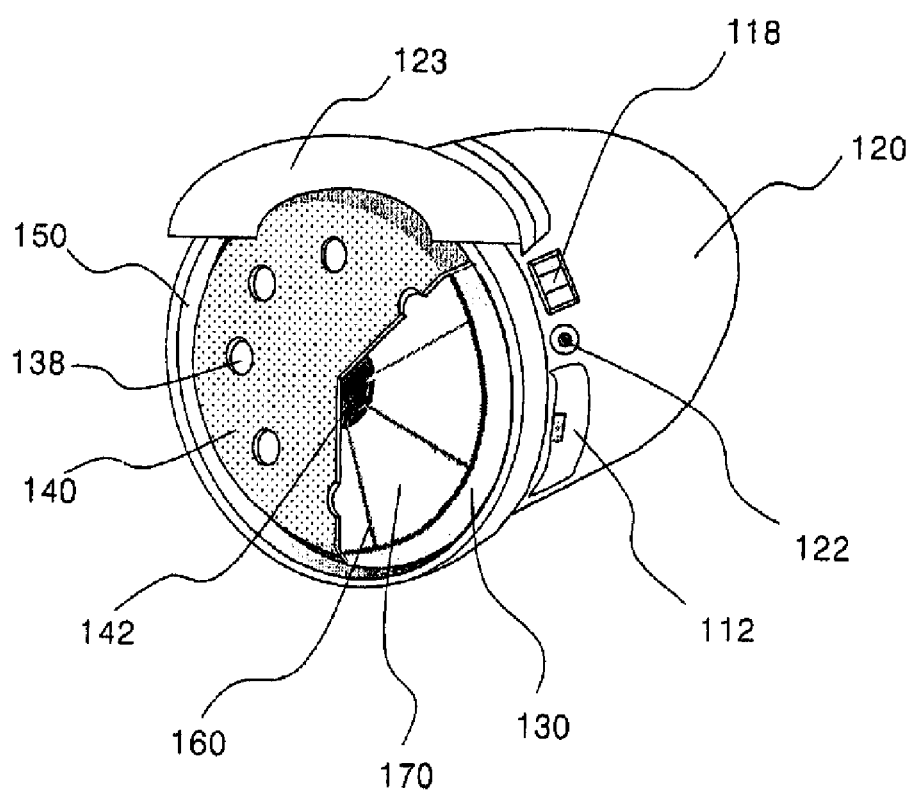
[Fig. 23]

ELECTRICAL DERMABRASION DEVICE

TECHNICAL FIELD

The present invention relates to an electrical dermabrasion device; and, more particularly, to an electrical dermabrasion device for removing a hard, dry skin layer on a heel, a sole, a lateral surface and toes of the foot by abrading them.

BACKGROUND ART

In general, the human skin can be divided into soft and hard areas. For example, a face or a hand directly exposed to the air without contacting other objects are soft, and a leg or a breast on which no strong pressure is imposed are also apt to be soft though they are not directly exposed to the air by being covered with cloths. In contrast, the skin of a foot comes into a direct contact with a hard surface of shoes for a long time while a person stands or walks, so a part of the foot skin becomes hardened, forming a dry, hardened layer of the skin. This dry, hardened skin layer is thickened with the lapse of time, or even cracked. In case the hardened layer of the skin cracks, a person may feel painful and there is a high likelihood that the wound is infected by the invasion of germs in the cracks.

Referring to FIG. 1, there is shown a conventional dermabrasion device 2. With the conventional dermabrasion device 2 as shown therein, a user has to get rid of a hardened layer of skin on foot by grasping a handle 4 firmly and using an abrasion plate 8 provided at one or both sides of a main body 6 of the device 2.

DISCLOSURE OF INVENTION

Technical Problem

In such a configuration, since the user has to move his/her hand repetitively in order to rub the device 2 over the hardened skin, an old or a weak person may become tired easily with the use of the conventional dermabrasion device 2. Further, the conventional dermabrasion device 2 also has a drawback in that the removed pieces of skin are dispersed all around, causing a sanitary problem. Moreover, most of the conventional dermabrasion devices are without covers, which results in poor appearance and inconvenience in carrying them.

Technical Solution

It is, therefore, an object of the present invention to provide an electrical dermabrasion device capable of exfoliating a hardened skin layer of, e.g., a foot effectively by using abrasion protrusions formed on an abrasion plate which is rotated by a motor.

In accordance with a first preferred embodiment of present invention, there is provided an electrical dermabrasion device includes: a main body provided with a hollow portion; an abrasion unit connected to the main body, for a dermabrasion; and a driving unit incorporated in a hollow portion of the main body, for rotating the abrasion unit, wherein the abrasion unit has a rotary plate, an abrasion plate attached to a front surface portion of the rotary plate and provided with a plurality of suction holes for suctioning exfoliated skin pieces resulted by the dermabrasion, and a connection frame connected to the main body while accommodating therein the rotary plate and the abrasion plate.

Advantageous Effects

As described above, the electrical dermabrasion devices in accordance with the present invention can solve the problems of the conventional dermabrasion device. That is, since the conventional dermabrasion device has to be rubbed over the skin repetitively using a physical force of a user, the user feels tired easily. Since, however, the inventive dermabrasion device is electrically operated by using the motor, it is unlikely that the user feels exhausted even after a long-time use thereof. Further, the time required for the exfoliation can be greatly reduced due to the high-speed rotation of the motor, and the dispersion of exfoliated skin pieces can be minimized by collecting them in the skin piece storages in the rotary plate or the skin pieces collecting vessel, thereby exhibiting a sanitary advantage. Moreover, by providing the cover for closing the main body, the contamination of the abrasion plate to be brought into contact with the skin can be prevented while facilitating the transporting of the dermabrasion device.

BRIEF DESCRIPTION OF THE DRAWINGS

The above and other objects and feature of the present invention will become apparent from the following description of preferred embodiments given in conjunction with the accompanying drawings, in which:

FIG. 1 is a perspective view of a conventional dermabrasion device;

FIG. 2 sets forth an exploded perspective view of an electrical dermabrasion device in accordance with a first preferred embodiment of the present invention;

FIG. 3 presents a view for setting forth components of the electric dermabrasion device shown in FIG. 2;

FIG. 4 depicts a perspective view of the electrical dermabrasion device shown in FIG. 2 in which a cover is separated from a main body thereof;

FIG. 5 provides a perspective view of the electrical dermabrasion device shown in FIG. 2 in which the cover is connected to the main body;

FIG. 6A is a plan view of a guard ring of the electric dermabrasion device shown in FIG. 2;

FIGS. 6B to 6D are side views showing the guard ring shown in FIG. 6A as viewed from different directions;

FIG. 7 offers a side view of a planar rotary plate and a planar abrasion plate for use in the electrical dermabrasion device shown in FIG. 2;

FIG. 8 shows a side view of an elliptical rotary plate and an elliptical abrasion plate for use in the electrical dermabrasion device shown in FIG. 2;

FIG. 9 is an enlarged view showing a part of the surface of the abrasion plate shown in FIG. 7 or 8;

FIG. 10 exemplifies an anti-slipping member and an equipment storage installed in the main body of the dermabrasion device shown in FIG. 2;

FIG. 11 shows a modification of the main body which is has a hand-holdable shape;

FIG. 12 sets forth an exploded perspective view of an electrical dermabrasion device in accordance with a second preferred embodiment of the present invention;

FIG. 13 illustrates various shapes of a rotary plate and an abrasion plate shown in FIG. 12;

FIG. 14 provides a side view of the electrical dermabrasion device shown in FIG. 12;

FIG. 15 depicts a front view of the electrical dermabrasion device shown in FIG. 12;

FIG. 16 provides a stereogram of the electrical dermabrasion device shown in FIG. 12;

FIG. 17 exemplifies one of various abrasion protrusions of the electrical dermabrasion device shown in FIG. 12;

FIGS. 18A to 18D demonstrate examples of an abrasion unit of the electrical dermabrasion device shown in FIG. 12;

FIG. 19 presents an exploded perspective view of a rotary plate, an impeller and a motor shaft of the electrical dermabrasion device shown in FIG. 12;

FIG. 20 offers a plan view of the rotary blade and the motor shaft of the electrical dermabrasion device shown in FIG. 12;

FIG. 21 is an exploded perspective view of an electrical dermabrasion device in accordance with a third preferred embodiment of the present invention;

FIG. 22 provides a plan view showing a modification of a rotary plate shown in FIG. 21; and FIG. 23 shows a perspective view of the modification of the electrical dermabrasion device in FIG. 21.

BEST MODE FOR CARRYING OUT THE INVENTION

Referring to FIGS. 2 to 9, an electrical dermabrasion device 10 in accordance with a first preferred embodiment of the present invention will now be described. The electrical dermabrasion device 10 includes a hollow main body 12, an abrasion unit installed at one side of the main body 12 to be used to remove hardened skin, and a driving unit incorporated in the hollow portion of the main body to rotate the abrasion unit. The electrical dermabrasion device 10 may further include a cover 56 detachably attached to the main body 12 to selectively expose the abrasion unit.

Though the main body 12 is shown to have an approximately oval shape in this preferred embodiment, it is can form the main body 12 to have an elongated shape allowing a user to hold it conveniently, as shown in FIG. 11.

The abrasion unit includes a rotary plate 32, an abrasion plate 42 attached on the front surface of the rotary plate 32 and a connection frame 48 to be engaged with the main body 12 via screw threads 28 while accommodating the rotary plate 32 and the abrasion plate 42 therein. The abrasion plate 42 is provided with a plurality of suction holes 44 for suctioning exfoliated skin pieces when the abrasion plate 42 is rubbed away over the hardened skin. Further, disposed between the rotary plate 32 and the abrasion plate 42 is a magnet 40 which serves to prevent the separation of the abrasion plate 42 from the rotary plate 32 when the rotary plate 32 is rotated at a high speed. The abrasion plate 42 is also provided at its outer periphery with a plurality of hooks 46 to be hooked with hook recesses 34 formed at the rotary plate 32. Meanwhile, the rotary plate 32 is partitioned into several skin piece storages 36 for storing therein the exfoliated skin pieces.

The connection frame 48 has a fixing portion 52 provided with a circular insertion groove. By fitting a lower part of a guard ring 54 into the fixing portion 52, the guard ring 54 is joined with the connection frame 48, while preventing the exfoliated skin pieces from being dispersed. Preferably, the guard ring 54 is configured such that its height is variable.

Specifically, FIG. 6A provides a plan view of the guard ring 54 adjoined with the fixing portion 52 of the connection frame 48 and FIGS. 6B to 6D present side views thereof obtained from different directions. As can be seen from FIGS. 6A to 6D, if the height of the guard ring 54 is low at one side and gradually increases toward the opposite side, the amount of exfoliated skin pieces dispersed out of the higher portion of the guard ring 54 is small. Therefore, in order to prevent the exfoliated skin pieces from dispersing toward the face of the user, the higher portion of the guard ring 54 needs to be located closer to the face. In case of setting the height of the guard ring 54 to be great entirely, efficient exfoliation can not be accomplished when, for example, exfoliating a flat skin portion such as a sole of the foot because the flat skin portion comes into contact with the edge portion of the guard ring 54 first, not the abrasion plate 42. Therefore, it is preferable to determine the height of the guard ring 54 within a range without incurring such a problem.

The connection frame 48 is provided with a plurality of protrusions 50 at one side thereof. The protrusions 50 are fitted into engagement holes 58 formed inside the cover 56 when the cover 56 is adjoined with the main body 12, so that the cover 56 is prevented from shaking or being separated from the connection frame 48. Though the coupling of the cover 56 and the connection frame 48 is achieved by inserting the protrusions 50 into the engagement holes 58 in this preferred embodiment, it is to be noted that a means to couple them is not limited thereto.

As shown in FIG. 7, the rotary plate 32 and the abrasion plate 42 may be of planar shapes and the abrasion plate 42 may be positioned such that it is protruded higher than the top end of the connection frame 48 by height A. Alternatively, the rotary plate 32 and the abrasion plate 42 may be formed to have elliptical shapes such that the abrasion plate 42 arches upward higher than the top end of the connection frame 48 by height B, as illustrated in FIG. 8. In any of cases, it is possible to exfoliate a wide, flat skin area such as a sole and an instep of the foot effectively. Though not shown, it is also possible to form the rotary plate 32 and the abrasion plate 42 to have conic shapes.

The abrasion plate 42 can be fabricated by using, e.g., metal corrosion, electric casting and polishing sand. Among these, the metal corrosion is most widely employed due to its advantages of simple manufacturing process, low cost and high effectiveness. In case of employing the metal corrosion, how to shape abrasion protrusions 60 of the abrasion plate 42 becomes important.

FIG. 9 shows an example of the abrasion protrusions 60. In case of forming the abrasion protrusions 60 to have polygonal shapes such as triangular and rectangular shapes, it is preferable to make their edge portions sharp to facilitate exfoliation. It is also possible to vary the shapes of the abrasion protrusions 60 depending on the rotational speed or the power of a motor 14 to obtain an optimum exfoliating effect. The abrasion protrusions 60 can also be of circular shapes or even formless, and it is also possible to make the abrasion protrusions 60 locally have different shapes even on the single abrasion plate 42.

FIG. 17 shows another example of abrasion protrusions. Each abrasion protrusion 146 shown therein has a shape in which a surface portion 146a thereof has a triangular structure with three apexes 146c, 146d and 146e. The sharp sides of the apexes 146c, 146d and 146e powerfully exfoliate the skin while being rotated. Further, the height of lateral portions 146b of each abrasion protrusion 146 concerns the exfoliating performance. Therefore, for the purpose of exfoliating the skin of the foot effectively, it is preferable to prepare several abrasion plates 140 with abrasion protrusions 146 different from each other in shapes, heights (depths) and arrangements and to use one of them depending on the state of the hardened skin on the foot.

The main body 12 has therein the motor 14 serving as a driving unit, a reduction gear box 16, a motor shaft 18 engaged with the reduction gear box 16, a control switch 20 for controlling the rotational speed of the motor 14, a jack 22, a luminous body 24 and a resistor 30. When the electrical dermabrasion device 10 in accordance with the present invention is driven by converting a household AC power into a DC power, an adopter is require, wherein one end of the adapter is connected to a household power supply while the other is connected to the jack 22 of the electrical dermabrasion device, to thereby supply a power for use in driving the motor 14. The power for the driving of the motor 14 can also be supplied from a battery or can be supplied from the household power supply directly. In such cases, the supply of power can be performed without the jack 22.

The luminous body 24 emits light through a transparent plate 26 when power is supplied to the electrical dermabrasion device 10 or the motor 14 is driven, to thereby allow the user to confirm the supply of the power conveniently. The luminous body 24 can be a bulb, an LED, a high-luminance LED, or the like, but is not limited thereto. The switch 20 controls the operation of the motor 14 by enabling or disabling the supply of the power to the motor 14. Further, by installing the resistor 30 at one side of the motor 14, a speed control of the motor 14 is enabled. Though not shown in the drawings, a resistor can be installed at one side of the luminous body 24 depending on types and standards of the luminous body 24. Further, though the components in the main body 12 of the electrical dermabrasion device 10 are interconnected via plural electric wires, the illustration of the electric wires is omitted in the drawings for the simplicity thereof.

The rotary plate 32 is driven to rotate by the motor 14. In order to increase the power of the motor 14 while reducing the rotational speed thereof, the motor shaft 18 is connected to the center of the motor 14 with the reduction gear box 16 interposed therebetween. Further, in order to prevent a free rotation of the rotary plate 32, a rear central portion of the rotary plate 32 is engaged with a cut-off portion of the motor shaft 18, so that the rotary plate 32 is made to rotate at the same speed as that of the motor shaft 18 when the motor shaft 18 rotates. Here, the reduction gear box 16 can be omitted, if necessary.

Operation of the electrical dermabrasion device with the above-described configuration will now be described. After power is supplied via the adapter (not shown), the switch 20 is turned on to drive the motor 14. As the motor 14 is driven, the motor shaft 18 is rotated, and the rotary plate 32 engaged with the motor shaft 18 is also rotated. Along with the rotation of the rotary plate 32, the abrasion plate 42 mounted on top of the rotary plate 32 is also rotated, so that hardened skin is exfoliated by the abrasion protrusions 60 of the abrasion plate 42. Some of the exfoliated skin pieces are then collected in the skin piece storages 36 inside the rotary plate 32 through the suction holes 44 of the abrasion plate 42. Due to the presence of the guard ring 54 connected to the connection frame 48, the dispersion of the exfoliated skin pieces in a certain direction can be prevented. Upon the completion of the exfoliation, the connection frame 48 is separated from the main body 12 and the abrasion plate 42 is also separated from the rotary plate 32. Then, by slanting the main body 12 toward the ground, the skin pieces collected in the skin piece storages 36 are removed. It is also possible to empty the storages 36 by separating the rotary plate 32 and the abrasion plate 42 from the motor shaft 18 and then separating the abrasion plate 42 from the rotary plate 32. After removing the exfoliated skin pieces, the rotary plate 32, the abrasion plate 42, the connection frame 48 and the guard ring 54 are reassembled to the main body 12. Then, by closing them with the cover 56, the abrasion plate 42 is protected from contamination. The presence of the cover 56 also provides good appearance of the dermabrasion device 10 and facilitates the transporting thereof.

As shown in FIG. 10, provided at one side of main body 12 is a plurality of anti-slipping plates 62, so the main body 12 is prevented from being slipped out of the user hand when the user abrades the hardened skin by grasping the main body 12. Further, provided at the other side of the main body 12 is an equipment storage 64 for storing therein a brush for cleaning, an ointment for skin protection, etc.

Moreover, as shown in FIG. 11, the main body 12 can be elongated in one direction to allow the user to hold it conveniently, thereby facilitating the exfoliation work. Further, by installing the jack 22 at the rear surface of the main body 12, an adopter line is kept such that it does not hinder the exfoliation work. Furthermore, though anti-slipping plates 62, the equipment storage 64, and so forth are not shown in FIG. 11, it is apparent that the electrical dermabrasion device in FIG. 11 can be configured to have them as in FIG. 10.

Referring to FIGS. 12 to 20, there is illustrated an electrical dermabrasion device 100 in accordance with a second preferred embodiment of the present invention. As shown therein, the electrical dermabrasion device 100 includes a hollow main body 120 having a handle 110 attached thereto, an abrasion unit installed at one side of the main body 120 to remove hardened skin, and a driving unit incorporated in the hollow portion of the main body 120 to rotate the abrasion unit. Though not shown, the electrical dermabrasion device 100 may further include a cover detachably connected to the main body 120 to selectively expose the abrasion unit, as in the above-described first embodiment of the present invention.

As in the first embodiment, the main body 120 is of an oval shape, and the handle 110 is attached to a lower portion thereof. Further, the inside of the handle 110 is utilized as a brush storage 112 for storing therein a brush for cleaning, etc.

The driving unit includes a first motor 114 for rotating a first impeller 132, a second motor 116 for rotating a second impeller 134, a control switch 118 for controlling the rotational speed of the first and the second motor 114 and 116, an adapter coupling connector 122, and so forth.

The abrasion unit includes a rotary plate 130, an abrasion plate 140 attached on the front surface of the rotary plate 130 to exfoliate the skin, and an external frame 150 to be adjoined to the front portion of the main body 120 while accommodating the rotary plate 130 and the abrasion plate 140 therein such that they are rotable.

Disposed at a central portion of the rotary plate 130 is a magnet 142 which serves to prevent the abrasion plate 140 from being separated from the rotary plate 130. Furthermore, a plurality of hooks 148 formed at the periphery of the abrasion plate 140 are fitted into hook recesses 144 provided at the periphery of the rotary plate 130 and maintained in place, so the separation of the abrasion plate 140 from the rotary plate 130 can be prevented during a rapid rotation of the rotary plate 130.

The external frame 150 is provided with a screw thread (not shown) at the inner surface thereof, and the screw thread of the external frame 150 is engaged with another screw thread 121 formed at the main body 120. Thus, even in case the abrasion plate 140 is separated from the rotary body 130 in spite of the magnetic force of the magnet 142 and the fixing force by the hooks 148, the abrasion plate 140 is blocked by the external frame 150. As a result, the abrasion plate 140 is prevented from being disintegrated from the dermabrasion device 100 completely. In addition, the main body 120 has at one side a guard ring 123, wherein the guard ring 123 prevents skin pieces exfoliated from, e.g., the foot from being dispersed in all directions.

Each of the rotary plate 130 and the abrasion plate 140 can have, for example, a planar, an elliptical or a truncated conic shape, as illustrated in FIGS. 13 and 18. Particularly, as for the shape of the abrasion plate 140, a truncated conic shape 140*a* or an elliptical shape 140*b* protruded higher than the external frame 150 is more effective in exfoliating a wide, flat skin portion, e.g., the sole of the foot compared to a planar shape 140*c*. To be specific, with the abrasion plate 140 of the planar shape 140*c*, it is difficult to effectively exfoliate the wide, flat skin portion, e.g., the sole of the foot because the abrasion plate 140 of the planar abrasion plate 140*c* is located inside the external frame 150. However, in case of using an abrasion plate 140 of a protruding planer shape 140*d* which protrudes forward higher than the external frame 150, the same effect as obtained with the elliptical or the truncated conic shape 140*b* or 140*a* can be attained. Further, it is preferable that the rotary plate 130 is formed to be matched with the abrasion plate 140. Specifically, when the shapes of the abrasion plate 140 are of the truncated conic shape 140*a*, the elliptical shape 140*b*, the planar shape 140*c* and the protruded planar shape 140*d* respectively, the rotary plate 130 is also formed to have a truncated conic shape 130*a*, an elliptical shape 130*b*, a planar shape 130*c* and a protruded planar shape 130*d*.

Through-holes 138 are formed through the rotary plate 130 and the abrasion plate 140. The skin pieces exfoliated from the foot is sent to a skin piece collecting filter 126 of a skin piece collecting vessel 124 through the through-holes 138. The skin piece collecting vessel 124 is detachably connected to the main body 120 by fitting a pair of fixing shafts rods 135 provided at one side of the skin piece collecting vessel 124 to each of the engagement grooves 137 formed at one side of the main body 120. Accordingly, if the skin piece collecting filter 126 is filled with the exfoliated skin pieces, it is possible to separate the skin piece collecting vessel 124 from the main body 120 and clean the skin piece collecting vessel 124 and the skin piece collecting filter 126 therein. Further, provided at one side of the skin piece collecting vessel 124 is a number of air holes 131 through which air suctioned by the rotary force of the first and the second impeller 132 and 134 flows into skin piece collecting filter 126 to be released outside. By such an air flow, the exfoliated skin pieces are moved in the suctioning direction of the air to be collected in the skin piece collecting filter 126.

Meanwhile, if the rotary plate 130 is rotated by the rotation of the first motor 114, the abrasion plate 140 detachably attached thereto is also rotated. Concurrently, by the rotation of the first impeller 132 attached to a first motor shaft 136 of the first motor 114, the skin pieces exfoliated from the foot are moved by the suctioning force of the first impeller 132 in a direction toward the first impeller 132 to be collected in the skin piece collecting filter 126 of the skin piece collecting vessel 124. Likewise, if the second impeller 134 attached to a second motor shaft 136 of the second motor 116 is rotated by the rotation of the second motor 116, the skin pieces exfoliated from the foot are moved by the suctioning force of the second impeller 134 in a direction toward the second impeller 134 to be collected in the skin piece collecting filter 126 of the skin piece collecting vessel 124. At this time, the rotation number of the second motor 116 per unit time is greater than that of the first motor 114, so the second motor 116 functions as a main motor for the suctioning of the exfoliated skin pieces while the first motor 114 serves as an assistant motor. As described, by using two motors and two impellers, the suctioning force can be enhanced considerably.

Referring to FIGS. 19 and 20, formed at one end of the first motor shaft 136 of the first motor 114 is a plurality of fitting protrusions 123*a* for use in detachably adjoining the rotary plate 130 to the first motor shaft 136 of the first motor 114. The other end of the motor shaft 136 is provided with a fixing support 123*b* serving to fix the motor shaft 136 in places. The first impeller 132 is provided with an impeller shaft 114*a* having a connection hole 114*c*, blades 114*b*, and an engagement opening 114*d*. The rotary plate 130 has a flange 139 with a hollow portion 139*a* at a central portion thereof. The fitting protrusions 123*a* formed at the first motor shaft 136 of the first motor 114 are fitted into the engagement opening 114*d* of the first impeller 132, whereby the first impeller 132 can be rotated by the rotation of the first motor shaft 136. The first impeller 132 and the first motor shaft 136 are detachable. The fixing support 123*b* serves to prevent the first impeller 132 from being fitted into the first motor shaft 136 too deeply. Likewise, the attachment/detachment of the second impeller 134 to/from the second motor shaft 136 of the second motor 116 can be achieved by using the same method as described in the case of attaching/detaching the first impeller 132 to/from the first motor shaft 136.

If the skin piece collecting filter 126 of the skin piece collecting vessel 124 is filled with the exfoliated skin pieces, the skin piece collecting vessel 124 is separated from the main body 120. Then, by removing the skin pieces from the skin piece collecting filter 126 in the skin piece collecting vessel 124, the skin piece collecting filter 126 is cleaned. Further, the skin piece collecting vessel 124 and the skin piece collecting filter 126 can be cleaned by the brush accommodated in the brush storage 112. In addition, with the brush, it is possible to clean most components of the electrical dermabrasion device 100, e.g., the first impeller 132, the second impeller 134, the rotary plate 130, the abrasion plate 140, the main body 120, and so forth.

The electrical dermabrasion device 100 with the above-described configuration in accordance with the second embodiment is operated as follows. If the switch 118 is turned on after supplying power using an adapter (not shown), the first and the second motor 114 and 116 are driven. By the rotation of the first motor 114, the first impeller 132 and the rotary plate 130 connected to the first motor shaft 136 are rotated, whereby the abrasion plate 140 installed on top of the rotary plate 130 is also rotated, so that exfoliation is performed. The switch 118 is used to control the rotational speed of the first motor 114 as well as to supply the power to the dermabrasion device 100. Thus, by adjusting the rotational speed of the abrasion plate 140 depending on the state of the to-be-exfoliated skin of the foot by means of the switch 118, effective exfoliation can be performed without causing a wound on the foot. Though the abrasion plate 140 is rotated at a high speed, it can be prevented from being separated from the rotary plate 130 due to the presence of the magnet 142 installed at the central portion of the rotary plate 130. Besides, in case the abrasion plate 140 is made of a metallic material, the rotary plate 130 and the abrasion plate 140 are firmly attracted to each other by the magnet 142. Moreover, by fitting the plurality of hooks 148 of the abrasion plate 140 into the hook recesses 144 of the rotary plate 130, the abrasion plate 140 can be secured to the rotary plate 130 firmly. In addition, by configuring the external frame 150 to enclose the outer periphery of the abrasion plate 140 when it is attached to the main body 120, the abrasion plate 140 can be prevented from being completely disintegrated from the electrical dermabrasion device 100 even though it is separated from the rotary plate 130. When the switch 118 is turned on, the second motor 116 as well as the first motor 114 is rotated, whereby the second impeller 134 connected to the second motor shaft 136 of the second motor 116 is also rotated, to thereby allow exfoliated skin pieces to be collected in the skin piece collecting filter 126 inside the skin piece collecting vessel 124. Since the abrasion plate 140 and the rotary plate 130 are respectively provided with the plurality of through-holes 138, the exfoliated skin pieces are moved toward the skin piece collecting vessel 124 therethrough. After separating the external frame 150 from the main body 120, the abrasion plate 140, the rotary plate 130, the first and the second impeller 132 and 134 and the skin piece collecting vessel 124 can be all separated from the first motor shaft 136. Therefore, after using the electrical dermabrasion device 100 for a certain period of time, the components can be cleaned using the brush accommodated in the brush storage 112 within the handle 110. Moreover, by preparing several abrasion plates 140 having different surface roughness, it is possible to select one of them depending on the state of the skin of the foot to be exfoliated. The guard ring 123 installed at one side of the main body 120 is configured to be positioned toward the body or the face of the user when the dermabrasion device is used, to thereby allow the exfoliated skin pieces to fall in a direction opposite to the face or the body, i.e., mainly downward without being dispersed toward the face or the body of the user.

Referring to FIGS. 21 to 22, there is described an electrical dermabrasion device in accordance with a third preferred embodiment of the present invention. As shown therein, instead of forming holes through a rotary plate 130, a plurality of ribs 160 is installed inside the rotary plate 130, and skin piece storages 170 capable of collecting exfoliated skin pieces therein are prepared therebetween by forming grooves between the ribs 160. Accordingly, exfoliated skin pieces are collected in the skin piece storages 170, so the second motor 116, the skin piece collecting vessel 124, the skin piece collecting filter 126, and the first and second impeller 132 and 134 as described in the second embodiment can be omitted.

While exfoliating the foot with the electrical dermabrasion device, some of exfoliated skin pieces are moved inside the abrasion plate 140 through through-holes 138 of the abrasion plate 140, and most of these skin pieces are collected in the skin piece storages 170 within the rotary plate 130 while some of them are dispersed. However, the dispersed skin pieces become to collide with the guard ring 123 and fall downward. In accordance with the third embodiment, by modifying only the shape of the rotary plate 130, a cost-effective electrical dermabrasion device capable of removing hardened skin from, e.g., the foot can be obtained. Since the configuration of the third embodiment is identical to those of the other two embodiments except the above-described structure, detailed description thereof will be omitted.

FIG. 23 provides a stereogram of a modification of the electrical dermabrasion device in accordance with the third embodiment, wherein the handle 110 is removed. As can be seen therefrom, a switch 118, a brush storage 112 and a connector 122 are installed at a same side of a main body 120, so the structure of the electrical dermabrasion device becomes simpler and the manufacturing costs can be reduced. Since the configuration of the electrical dermabrasion device shown in FIG. 12 is identical to that of the above-descried electrical dermabrasion device in accordance with the third embodiment except the absence of the handle 110, detailed description thereof will be omitted.

While the invention has been shown and described with respect to the preferred embodiments, it will be understood by those skilled in the art that various changes and modifications may be made without departing from the spirit and scope of the invention as defined in the following claims.

The invention claimed is:

1. An electrical dermabrasion device comprising:
a main body provided with a hollow portion;
an abrasion unit connected to the main body, for a dermabrasion;
a driving unit including a motor incorporated in a hollow portion of the main body, for rotating the abrasion unit, wherein the abrasion unit includes a generally planar rotary plate and a generally planar abrasion plate removably attached to a front surface portion of the rotary plate, the abrasion plate having a generally planar abrading surface which is generally perpendicular to an axis of rotation of the abrasion plate, the abrading surface is provided with a plurality of suction holes for suctioning exfoliated skin pieces resulting from the dermabrasion, the rotary plate including a plurality of discrete radially extending partitions forming skin piece storages for collecting therein the exfoliated skin pieces suctioned through the suction holes of the abrasion plate, the partitions including ribs and the storages include grooves formed between the ribs, the abrasion unit further including a connection frame removably securable to the main body, the connection frame accommodating therein the rotary plate and the abrasion plate; and
a guard ring installed at an upper portion of the main body to prevent a dispersion of the exfoliated skin pieces, the guard ring having a first side and a second side opposite the first side with the abrasion plate disposed between the first and second side, wherein a height of the guard ring varies from the first side to the second side, such that the first side is higher than the second side, and wherein the guard ring has a top surface defining an upper extent of the guard ring, and the top surface at the first side of the guard ring is disposed above the abrading surface.

2. The dermabrasion device of claim 1, wherein a magnet is disposed between the rotary plate and the abrasion plate to serve to prevent the separation of the abrasion plate from the rotary plate.

3. The dermabrasion device of claim 1, wherein the driving unit includes a control switch for controlling an operation and a rotational speed of the motor, and a connector for connecting the motor to a power supply.

4. The dermabrasion device of claim 1, wherein the motor rotates a first impeller, and the driving unit includes an additional motor for rotating a second impeller, a control switch for controlling operations and rotational speeds of the motors, and an adapter coupling connector for a power supply.

5. The dermabrasion device of claim 1, further comprising a cover detachably attached to the main body, for selectively exposing the abrasion unit.

6. The dermabrasion device of claim 1, wherein the abrasion plate is fabricated by using a metal corrosion, an electric casting or polishing sand.

7. The dermabrasion device of claim 1, wherein the abrasion plate is provided with a plurality of abrasion protrusions and each abrasion protrusion is of a polygonal shape with a sharpened edge portion.

8. The dermabrasion device of claim 1, wherein the main body is provided with an anti-slipping member.

9. The dermabrasion device of claim 1, wherein the main body is provided with an equipment storage for storing therein an equipment.

10. The dermabrasion device of claim 2, wherein the abrasion plate is disposed such that an abrasion surface thereof is located higher than a top end of the connection frame.

11. The dermabrasion device of claim 1, wherein the main body has a hand-holdable shape.

12. The dermabrasion device of claim 1, further comprising a handle attached to the main body.

13. The dermabrasion device of claim 1, wherein the rotary plate includes suction holes and the suction holes of the abrasion plate and rotary plate permit exfoliated skin pieces to pass therethrough, the dermabrasion device further including a skin piece collecting vessel disposed downstream of the rotary plate for collecting therein the exfoliated skin pieces suctioned through the suction holes of the rotary plate and the abrasion plate.

14. The dermabrasion device of claim 13, wherein the skin piece collecting vessel incorporates a skin piece collecting filter therein and is provided with air holes for allowing suction air to pass therethrough.

15. The dermabrasion device of claim 1, wherein the main body incorporates therein a power supply for driving the driving unit.

16. The dermabrasion device of claim 1, wherein the roughness of the abrasion plate is varied depending on the state of hardened skin to be exfoliated.

17. The dermabrasion device of claim 1, wherein the roughness of the abrasion plate is locally different.

18. The dermabrasion device of claim 1, wherein the height of the guard ring tapers from the first side to the second side.

19. The dermabrasion device of claim 1, wherein the height of the guard ring varies along an annular extent of the guard ring.

20. The dermabrasion device of claim 1, wherein the abrasion plate is disposed in a first plane and the guard ring upper surface is disposed in a second plane which is angularly offset from the first plane.

21. The dermabrasion device of claim 20, wherein the abrasion plate has an axis of rotation which is substantially perpendicular to the first plane.

22. The dermabrasion device of claim 1, wherein the guard ring surrounds a perimeter of the abrasion plate.

23. The dermabrasion device of claim 1, wherein the guard ring has a diameter which is greater than a maximum height of the guard ring.

24. The dermabrasion device of claim 1, wherein the suction holes include discrete apertures extending through a thickness of the abrasion plate.

25. The dermabrasion device of claim 24, wherein the suction holes are disposed on the abrasion plate in an annular pattern.

26. The dermabrasion device of claim 1, wherein the rotary plate discrete radially extending partitions include a linear extent extending from a central position of the plate to an outer periphery.

* * * * *